US012144957B2

(12) United States Patent
Akiyama

(10) Patent No.: US 12,144,957 B2
(45) Date of Patent: Nov. 19, 2024

(54) MEDICAL CONNECTOR

(71) Applicant: TERUMO KABUSHIKI KAISHA, Tokyo (JP)

(72) Inventor: Kazuya Akiyama, Kai (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 0 days.

(21) Appl. No.: 18/195,300

(22) Filed: May 9, 2023

(65) Prior Publication Data
US 2023/0277835 A1 Sep. 7, 2023

Related U.S. Application Data

(63) Continuation of application No. PCT/JP2021/037208, filed on Oct. 7, 2021.

(30) Foreign Application Priority Data

Nov. 12, 2020 (JP) ................. 2020-188903

(51) Int. Cl.
A61M 39/26 (2006.01)
A61M 39/10 (2006.01)

(52) U.S. Cl.
CPC ........... *A61M 39/26* (2013.01); *A61M 39/10* (2013.01); *A61M 2039/1033* (2013.01); *A61M 2039/266* (2013.01)

(58) Field of Classification Search
CPC ........... A61M 39/26; A61M 2039/266; A61M 2039/261; A61M 2039/262; A61M 2039/263; A61M 39/10; A61M 2039/1033
See application file for complete search history.

(56) References Cited

U.S. PATENT DOCUMENTS 5,163,922 A * 11/1992 McElveen, Jr. ........ A61M 39/02
604/905
5,676,346 A * 10/1997 Leinsing ............... A61M 39/26
604/905

(Continued)

FOREIGN PATENT DOCUMENTS

JP 2001-506156 A 5/2001
JP 2003144546 A * 5/2003 ............ A61M 39/26

(Continued)

OTHER PUBLICATIONS

International Searching Authority, "International Search Report," issued in connection with International Patent Application No. PCT/JP2021/037208, dated Nov. 22, 2021.

(Continued)

*Primary Examiner* — David Colon-Morales
(74) *Attorney, Agent, or Firm* — Foley & Lardner LLP

(57) ABSTRACT

A medical connector includes: a housing comprising a male connector attachment/detachment part, the housing defining a liquid flow path; and a valve that is vertically movable with respect to the housing between a closed position for closing the male connector attachment/detachment part, and an open position in which a flow path in a male connector communicates with the liquid flow path, by the valve being pressed down from the closed position by the male connector against a biasing force. The valve comprises a head portion that closes the male connector attachment/detachment part when the valve is at the closed position, and a body portion that is connected to a bottom end of the head portion and receives the biasing force. A Young's modulus of the body portion is larger than a Young's modulus of the head portion.

19 Claims, 10 Drawing Sheets

(56) References Cited

U.S. PATENT DOCUMENTS

| | | | | |
|---|---|---|---|---|
| 5,730,418 | A * | 3/1998 | Feith | A61M 39/26 604/905 |
| 6,039,302 | A * | 3/2000 | Cote, Sr. | A61M 39/26 604/905 |
| 6,228,069 | B1 * | 5/2001 | Barth | A61M 39/26 604/905 |
| 6,428,520 | B1 * | 8/2002 | Lopez | A61M 39/045 251/149.3 |
| 6,569,117 | B1 * | 5/2003 | Ziv | A61M 39/02 604/246 |
| 7,037,302 | B2 * | 5/2006 | Vaillancourt | A61M 39/26 604/905 |
| 7,396,348 | B2 * | 7/2008 | Newton | A61M 39/26 604/256 |
| 7,645,274 | B2 * | 1/2010 | Whitley | A61M 39/26 604/537 |
| 7,914,502 | B2 * | 3/2011 | Newton | A61M 39/045 604/246 |
| 8,105,314 | B2 * | 1/2012 | Fangrow, Jr. | A61M 39/26 604/533 |
| 9,107,987 | B2 * | 8/2015 | Chung | A61M 1/84 |
| 10,478,606 | B2 * | 11/2019 | Yang | A61M 39/24 |
| 11,123,534 | B2 * | 9/2021 | Chen | A61M 39/10 |
| 11,458,293 | B2 * | 10/2022 | Feith | A61M 39/02 |
| 2006/0163515 | A1 * | 7/2006 | Ruschke | A61M 39/26 251/149.7 |
| 2017/0014618 | A1 * | 1/2017 | Ueda | A61M 39/26 |
| 2017/0189665 | A1 * | 7/2017 | Ueda | A61M 39/1055 |
| 2018/0015278 | A1 * | 1/2018 | Ueda | A61M 39/26 |
| 2018/0021560 | A1 * | 1/2018 | Ueda | A61M 39/20 604/533 |
| 2019/0117953 | A1 * | 4/2019 | Ueda | A61M 39/1011 |
| 2020/0129750 | A1 | 4/2020 | Chen | |

FOREIGN PATENT DOCUMENTS

| | | |
|---|---|---|
| WO | WO-2015/145998 A1 | 10/2015 |
| WO | WO-2016/157886 A1 | 10/2016 |

OTHER PUBLICATIONS

International Searching Authority, "Written Opinion," issued in connection with International Patent Application No. PCT/JP2021/037208, dated Nov. 22, 2021.

International Searching Authority, "Written Opinion," issued in connection with International Patent Application No. PCT/JP2021/037208, dated Nov. 22, 2021 (with English translation).

* cited by examiner

MEDICAL CONNECTOR

CROSS-REFERENCE TO RELATED APPLICATIONS

This is a bypass continuation of PCT/JP2021/037208, filed on Oct. 7, 2021, which claims priority to Japanese Appl. No. JP2020-188903, filed on Nov. 12, 2020. The contents of these applications are hereby incorporated by reference in their entireties.

BACKGROUND

The present disclosure relates to a medical connector.

Conventionally, medical devices such as a catheter, a medical tube, and a syringe are connected to each other to form a liquid delivery line with a body cavity of a living body such as a human body, and liquid delivery such as infusion, blood transfusion, and artificial dialysis is performed through the liquid delivery line.

A medical connector described below is known as a medical connector for connecting medical devices in order to form the liquid delivery line described above. This medical connector includes: a housing which is provided with a male connector attachment/detachment part and forms a liquid flow path; and a valve which can be moved up and down with respect to the housing, between a closed position for closing the male connector attachment/detachment part and an open position that allows a flow path in a male connector to communicate with the liquid flow path by the valve being pressed down from the closed position by the male connector against a biasing force, wherein the valve includes a head portion which closes the male connector attachment/detachment part when the valve is in a closed state in which the valve is at the closed position, and a body portion which is connected to the bottom end of the head portion and receives the biasing force (see, for example, WO 2015/145998 A and WO 2016/157886 A).

SUMMARY

The medical connector is required to hardly generate a bolus or a backflow due to attachment and detachment of a male connector to and from the male connector attachment/detachment part. The bolus means that a liquid in the medical connector is expelled to the outside of the medical connector. The backflow means that a liquid outside the medical connector is drawn into the medical connector. For example, in a medical connector provided at a proximal end of a catheter, there is a possibility that blood drawn into the catheter from the living body by backflow is coagulated to form a thrombus, and the thrombus is administered from the inside of the catheter to the living body by a bolus.

In the medical connectors described in WO 2015/145998 A and WO 2016/157886 A, the body portion is formed of the same material as the head portion, and thus the body portion and the head portion are equally compressed at the open position. Accordingly, the medical connectors described in WO 2015/145998 A and WO 2016/157886 A are difficult to provide a structure that meets the above requirement.

In view of this, an object of the present disclosure is to provide a medical connector that easily provides a neutral structure which is less likely to generate a bolus and a backflow by an operation of attaching/detaching a male connector.

A medical connector according to one aspect of the present disclosure includes: a housing that is provided with a male connector attachment/detachment part and forms a liquid flow path; and a valve that is vertically movable with respect to the housing, between a closed position for closing the male connector attachment/detachment part and an open position that allows a flow path in a male connector to communicate with the liquid flow path by the valve being pressed down from the closed position by the male connector against a biasing force, wherein the valve includes a head portion that closes the male connector attachment/detachment part when the valve is in a closed state in which the valve is at the closed position, and a body portion that is connected to a bottom end of the head portion and receives the biasing force, and a Young's modulus of the body portion is larger than a Young's modulus of the head portion.

As one embodiment of the present disclosure, the valve includes an internal flow path that passes through at least the body portion and allows the flow path in the male connector to communicate with the liquid flow path in an open state in which the valve is at the open position.

As one embodiment of the present disclosure, the internal flow path is defined only by an inner surface of the valve.

As one embodiment of the present disclosure, the internal flow path has an open/close end that passes through the head portion and opens as the valve moves down.

As one embodiment of the present disclosure, the open/close end is formed as a slit.

As one embodiment of the present disclosure, the internal flow path has a side end that is open at a side face of the body portion.

As one embodiment of the present disclosure, the liquid flow path has a side opening that is open at a side face defining an accommodation chamber that accommodates the body portion in a vertically movable manner, and the side opening faces the side end of the internal flow path at least in the open state.

As one embodiment of the present disclosure, an upper portion of the side end communicates with the open/close end only through a lower portion of the side end that does not face the side opening in the open state.

As one embodiment of the present disclosure, the internal flow path includes two side ends that are open at the side face of the body portion, the liquid flow path includes two side openings that are open at the side face defining the accommodation chamber that accommodates the body portion in a vertically movable manner, one of the two side ends faces one of the two side openings in both the closed state and the open state, and another side end faces another side opening in both the closed state and the open state.

As one embodiment of the present disclosure, the two side ends are provided to be oriented in different directions.

As one embodiment of the present disclosure, the internal flow path includes a longitudinal flow path extending downward from the open/close end and a lateral flow path extending to both sides from a bottom end of the longitudinal flow path, and a lower surface of the lateral flow path has a protruding shape formed by two inclined surfaces inclined upward from the two side ends toward an inside of the valve.

As one embodiment of the present disclosure, the body portion includes a shoulder part extending laterally from the bottom end of the head portion.

As one embodiment of the present disclosure, the body portion has an upward protrusion to which the bottom end of the head portion is fitted.

As one embodiment of the present disclosure, an elastic member that generates the biasing force is provided.

The present disclosure can provide a medical connector that easily provides a neutral structure which is less likely to generate a bolus and a backflow by an operation of attaching/detaching a male connector.

DETAILED DESCRIPTION

Figure 1:
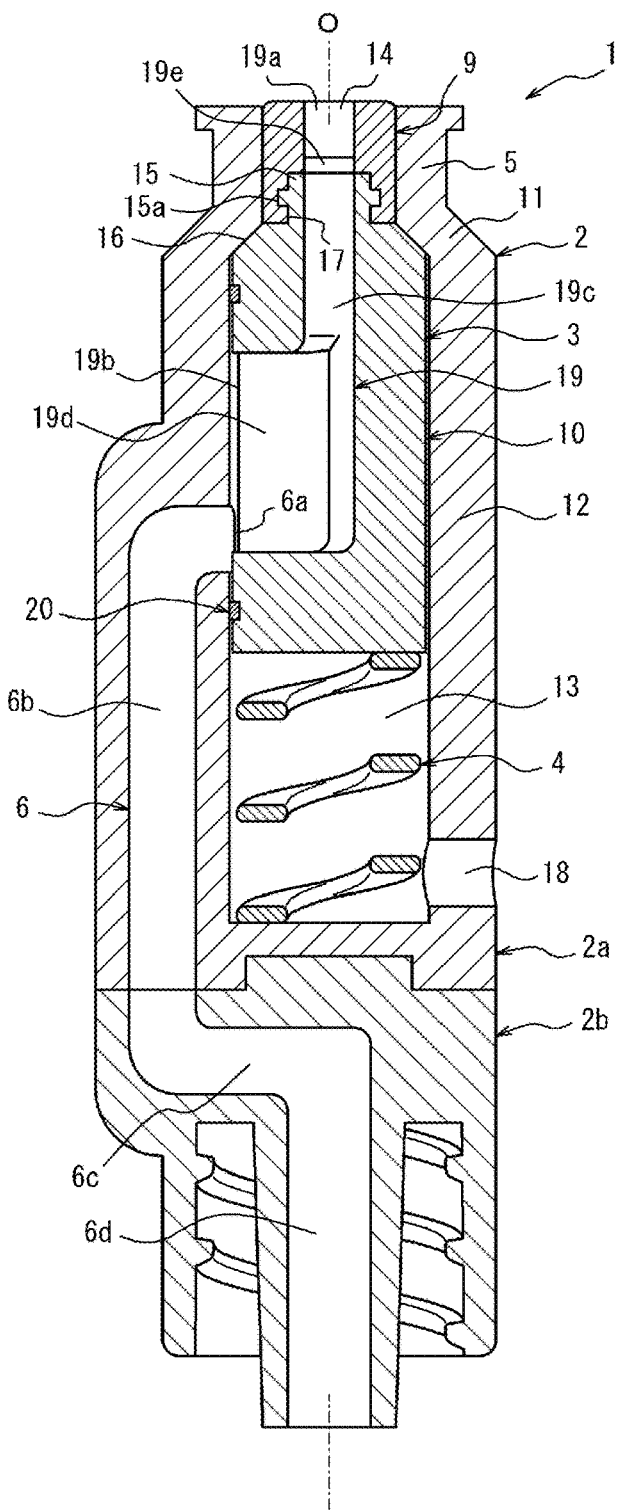
FIG. 1 is a cross-sectional view illustrating a medical connector as a first embodiment.

Embodiments of the present disclosure will be described in detail below with reference to the drawings. In the drawings, corresponding elements are denoted by the same reference numerals.

First, a medical connector 1 as a first embodiment will be described by way of example with reference to FIGS. 1 to 7. The medical connector 1 as the present embodiment illustrated in FIG. 1 includes a housing 2, a valve 3, and an elastic member 4. In addition, the medical connector 1 includes a male connector attachment/detachment part 5 to which a medical device can be connected in order that medical devices such as a medical tube or a syringe are connected to each other to form a liquid delivery line or the like with a body cavity of a living body such as a human body.

The housing 2 has the male connector attachment/detachment part 5 and forms a liquid flow path 6. The valve 3 can be moved up and down with respect to the housing 2, between a closed position (see FIG. 1) for closing the male connector attachment/detachment part 5 and an open position (see FIG. 7) that allows a flow path 8 in a male connector 7 (see FIG. 7) to communicate with the liquid flow path 6 by the valve 3 being pressed down (for convenience of description, the direction in which the valve is pressed down by the male connector 7 is referred to as a downward direction, and the direction opposite thereto is referred to as an upward direction) from the closed position by the male connector 7 against a biasing force. The valve 3 has a head portion 9 which closes the male connector attachment/detachment part 5 when the valve 3 is in a closed state in which the valve 3 is at the closed position, and a body portion 10 which is connected to the bottom end of the head portion 9 and receives the biasing force. The elastic member 4 generates the biasing force.

Figure 2:
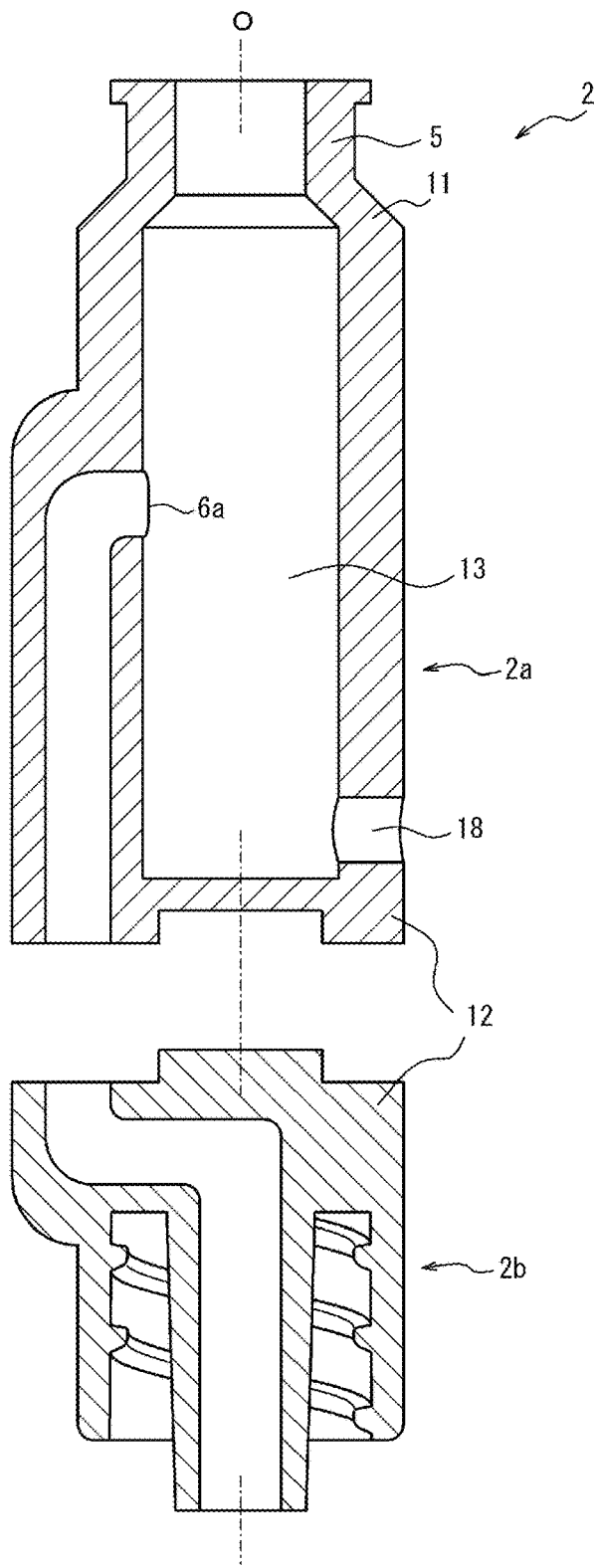
FIG. 2 is an exploded view of a housing illustrated in FIG. 1.
Figure 3:
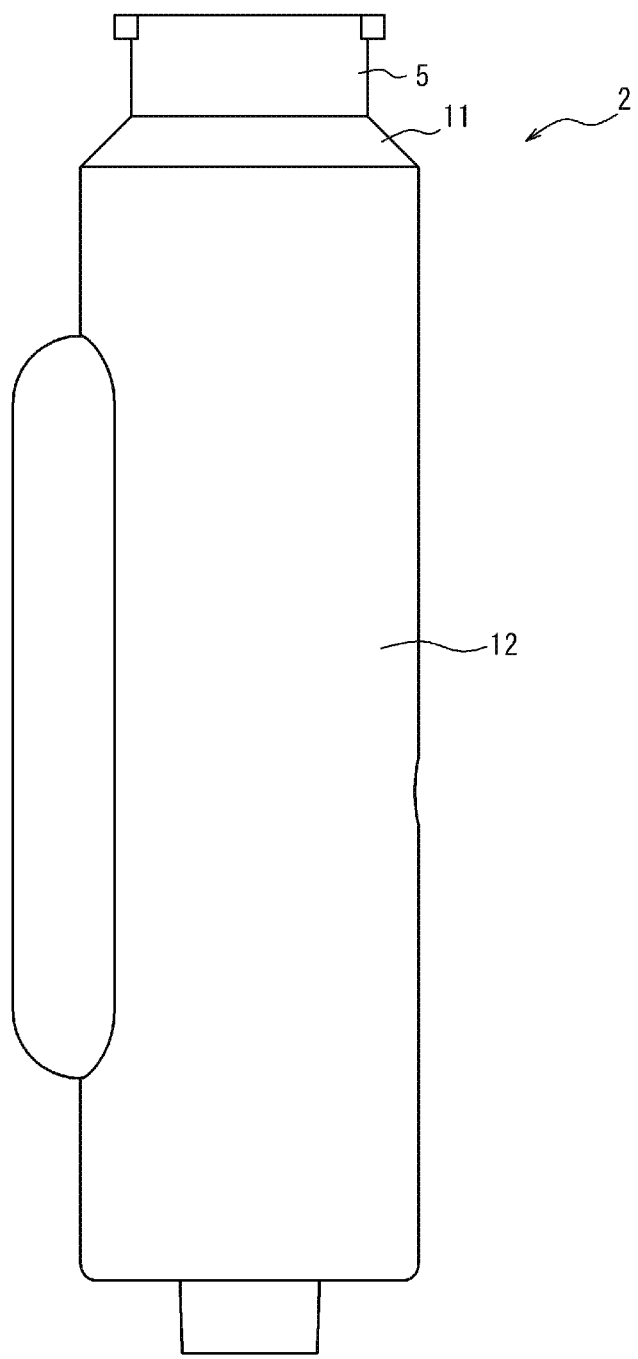
FIG. 3 is a side view of the housing illustrated in FIG. 1.

As illustrated in FIGS. 1 to 3, the housing 2 includes the cylindrical male connector attachment/detachment part 5 having an axis O extending along the vertical direction as a center thereof. A male connector 7 configured as a male luer lock connector can be attached to and detached from the male connector attachment/detachment part 5. The male connector attachment/detachment part 5 is configured to comply with, for example, ISO 80369-7 in 2016.

In the following description, a direction along a straight line orthogonal to the axis O is referred to as a radial direction, and a direction around the axis O is referred to as a circumferential direction.

A diameter-increased part 11 having a conical surface shape and flaring downward around the axis O is connected to a bottom end of the male connector attachment/detachment part 5. A housing main body 12 is connected to the bottom end of the diameter-increased part 11. The housing main body 12 forms an accommodation chamber 13 that accommodates the body portion 10 of the valve 3 in a vertically movable manner. The accommodation chamber 13 has a recessed shape defined by a cylindrical inner peripheral surface having the axis O as a center and a bottom surface.

As illustrated in FIG. 1, the housing main body 12 forms the liquid flow path 6. The liquid flow path 6 includes a side opening 6a which is open to a side face defining the accommodation chamber 13, a side flow path 6b extending downward along the accommodation chamber 13 from an upper end communicating with the side opening 6a to a bottom end below the accommodation chamber 13, a lower lateral flow path 6c extending radially inward from the bottom end of the side flow path 6b to an area below the accommodation chamber 13, and a lower longitudinal flow path 6d extending downward coaxially with the axis O from a radially inner end of the lower lateral flow path 6c.

A lower member 2b constituting the lower part of the housing main body 12 forms a male connector configured as a male luer lock having the bottom end of the side flow path 6b, the lower lateral flow path 6c, and the lower longitudinal flow path 6d therein. Therefore, the medical connector 1 is configured as an I-shaped connector. The male connector of the lower member 2b is configured to comply with, for example, ISO 80369-7 in 2016. As illustrated in FIG. 2, the housing 2 is formed by integrally connecting two components, that is, an upper member 2a and the lower member 2b, to each other by welding or the like. The lower member 2b may be formed as a medical device other than the male connector. The housing 2 may be constituted by a single component or three or more components. The housing 2 is formed of a hard material such as a synthetic resin.

Figure 4:
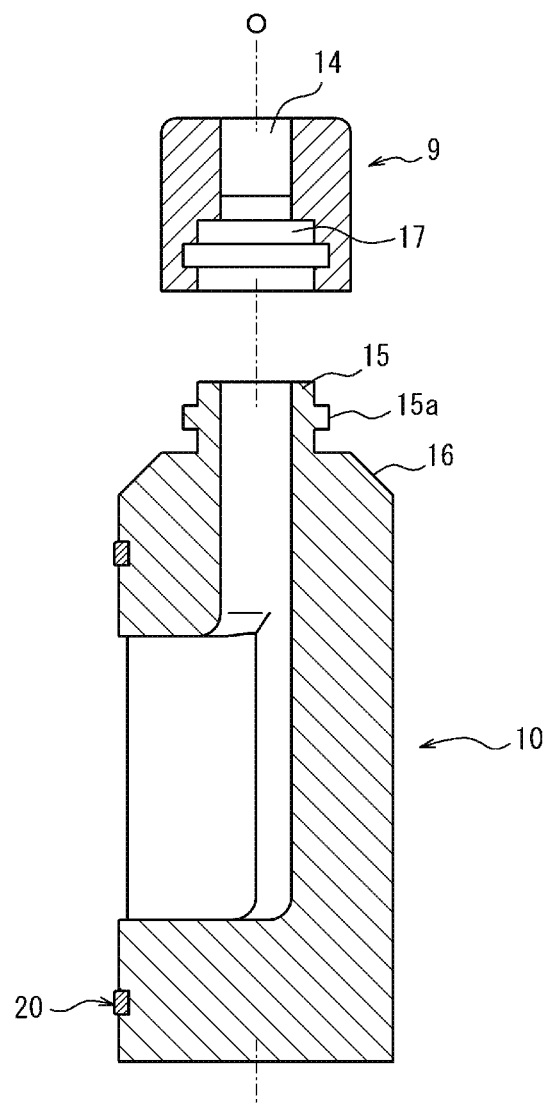
FIG. 4 is an exploded view of a valve illustrated in FIG. 1.
Figure 5:
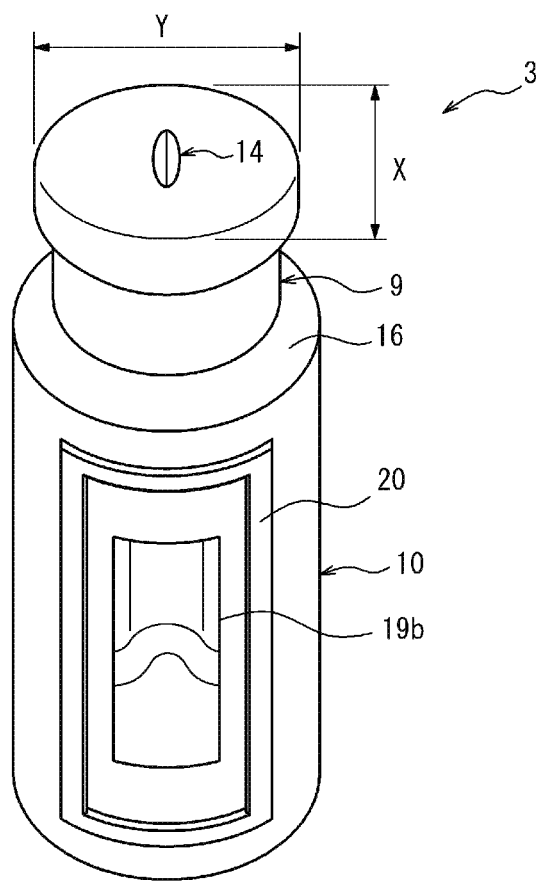
FIG. 5 is a perspective view of the valve illustrated in FIG. 1.

As illustrated in FIGS. 1, 4, and 5, the valve 3 includes the head portion 9 formed of an elastic material such as rubber or elastomer, and the body 10 portion formed of a hard material, for example, a synthetic resin such as polycarbonate, polypropylene, acrylonitrile butadiene styrene (ABS), or polyoxymethylene (POM).

The head portion 9 has a substantially cylindrical shape having the axis O as a center. The head portion 9 has a slit 14 that can be opened and closed. The slit 14 is provided at the center of the head 9 portion in top view, and is formed into a straight line shape orthogonal to the axis O in top view in a closed state. Both ends of the slit 14 in the length direction are separated from the outer peripheral edge of the head portion 9 at an equal distance in top view. The slit 14 penetrates the head portion 9 along the vertical direction.

The upper part of the head portion 9 has an elliptical shape in which a width Y in a direction perpendicular to the slit 14 is larger than a width X in a direction along the slit 14 in top view in a natural state before being elastically deformed. In addition, the slit 14 has an elongated elliptical shape in top view in a natural state. That is, the slit 14 is opened in a natural state to form a flow path through which liquid can pass. When the head portion 9 is pushed into the male connector attachment/detachment part 5 having a circular shape in top view, the head portion 9 is compressed in the Y direction, whereby the slit 14 is closed.

Note that the shapes of the slit 14 and the upper part of the head portion 9 are not limited to the above shapes. However, the slit 14 and the upper part of the head portion 9 preferably have a shape in which the slit 14 opens in a natural state and the slit 14 closes when the head 9 portion is pushed into the male connector attachment/detachment part 5.

The body portion 10 has a substantially columnar shape having the axis O as a center, and includes an upward protrusion 15 to which the bottom end of the head portion 9 is fitted, and a shoulder part 16 extending laterally from the bottom end of the head portion 9. The upward protrusion 15 protrudes from the upper surface of the body 10 portion and has a substantially columnar shape having the axis O as a center. The outer peripheral surface of the upward protrusion 15 has an annular protrusion 15a with the axis O as a center. The head portion 9 has, on the bottom surface, a recess 17 that has an inner peripheral surface having a complementary shape with respect to the outer peripheral surface of the upward protrusion 15. The recess 17 of the head portion 9 is fitted to the upward protrusion 15, by which the head portion 9 is held by the body portion 10. The shoulder part 16 has a conical surface shape having the axis O as a center and flares downward. An outer peripheral surface of the body portion 10 below the shoulder part 16 has a cylindrical shape.

The shape of the shoulder part 16 is not limited to the conical surface shape, and can be appropriately changed according to the shape of the inner peripheral surface of the diameter-increased part 11 of the housing 2.

Figure 6:
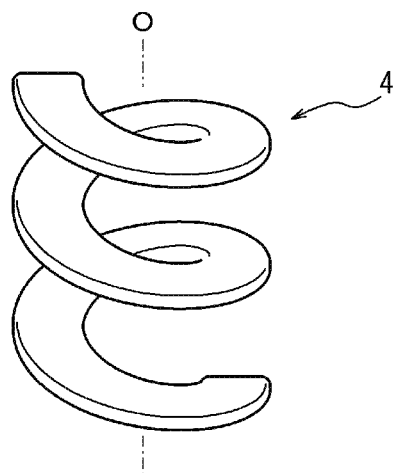
FIG. 6 is a perspective view of an elastic member illustrated in FIG. 1.

As illustrated in FIG. 6, the elastic member 4 is a coiled compression spring. As illustrated in FIG. 1, the elastic member 4 is disposed in the accommodation chamber 13 so as to be positioned between the bottom surface of the body portion 10 and the bottom surface of the accommodation chamber 13, and applies an upward biasing force to the bottom surface of the body portion 10. The elastic member 4 may be a compression spring having a shape other than a coil shape such as a bellows shape. The elastic member 4 is provided separately from the body portion 10. However, it may be formed integrally with the body portion 10 by, for example, two-color molding. The elastic member 4 is formed of, for example, a synthetic resin, rubber, elastomer, or a metal material such as stainless steel.

Figure 7:
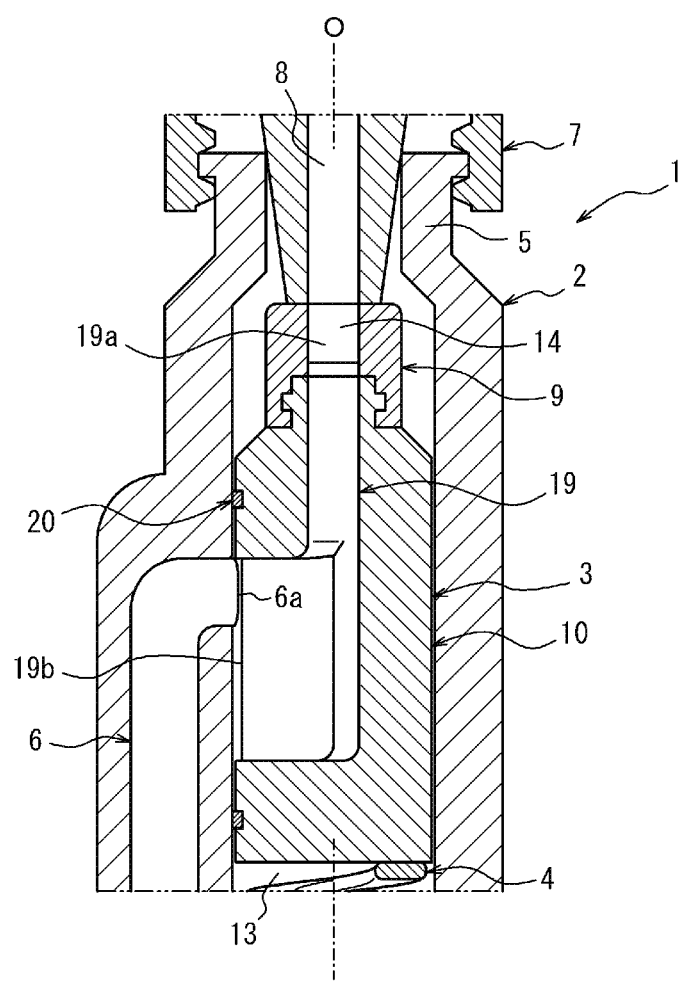
FIG. 7 is a cross-sectional view illustrating a state when a male connector is attached to the medical connector illustrated in FIG. 1.

As illustrated in FIGS. 1 and 7, the elastic member 4 generates a biasing force for returning the valve 3 from the open position to the closed position. An air hole 18 communicating with the outside of the medical connector is provided on the side face (peripheral surface) defining the accommodation chamber 13. While air in the accommodation chamber 13 is discharged from the air hole 18 with the downward movement of the valve 3, air is introduced into the accommodation chamber 13 through the air hole 18 with the upward movement of the valve 3, so that the valve 3 can be smoothly moved up and down. Note that the air hole 18 is not necessarily provided.

When the valve 3 moves down, the position of the downward movement limit of the valve 3 is determined by the bottom end (distal end) position of the male connector 7 when the male connector 7 is fitted to the male connector attachment/detachment part 5. When the valve 3 moves up, the position of the upward movement limit of the valve 3 is determined by the position where the shoulder part 16 comes in contact with the lower surface (inner peripheral surface) of the diameter-increased part 11 of the housing 2.

As illustrated in FIGS. 1 and 7, the valve 3 includes an internal flow path 19 that passes through both the head portion 9 and the body portion 10 and allows the flow path 8 in the male connector 7 to communicate with the liquid flow path 6 in the open state in which the valve 3 is at the open position. The internal flow path 19 is defined only by the inner surface of the valve 3. The internal flow path 19 has an open/close end 19a that passes through the head 9 portion and opens with the downward movement of the valve 3. The open/close end 19a is formed as the slit 14. The internal flow path 19 has a side end 19b (see FIGS. 5 and 7) which is open at the side face (outer peripheral surface) of the body portion 10.

The body portion 10 includes a longitudinal flow path 19c that extends downward along the vertical direction from the upper surface of the upward protrusion 15 at the center of the body portion 10 in top view, and a lateral flow path 19d that extends from the bottom end of the longitudinal flow path 19c to the side end 19b. The internal flow path 19 includes the open/close end 19a formed as the slit 14, a gap 19e between the upper surface of the upward protrusion and the lower surface of the head portion 9, the longitudinal flow path 19c, the lateral flow path 19d, and the side end 19b.

The side end 19b faces the side opening 6a of the liquid flow path 6 in both the closed state (see FIG. 1) and the open state (see FIG. 7). Note that the side end 19b may not face the side opening 6a in the closed state (see FIG. 1) but face the side opening 6a in the open state (see FIG. 7). In a case where the side end 19b and the side opening 6a do not face each other in the closed state, the pressure variation due to the deformation of the valve 3 is confined in the internal flow path 19, so that the pressure variation of the liquid flow path 6 is less likely to occur. Thus, a neutral structure can be more easily achieved.

As illustrated in FIGS. 1, 5, and 7, the body portion 10 includes a seal member 20 surrounding the side end 19b. The seal member 20 is integrally provided on the side face of the body portion 10, and slides in the vertical direction on the side face defining the accommodation chamber 13 as the valve 3 moves up and down. The seal member 20 can prevent leakage of the liquid in the internal flow path 19 and the liquid flow path 6 from the gap between the side face defining the accommodation chamber 13 and the side face of the body portion 10.

In the present embodiment, the Young's modulus (longitudinal elastic modulus) of the body portion 10 is larger than that of the head portion 9. Therefore, the present embodiment can easily achieve a structure in which the volume change of the liquid flow path (that is, the internal flow path 19 and the liquid flow path 6) in the medical connector 1 is small between the open state and the closed state, that is, a neutral structure which is less likely to generate a bolus and a backflow by an operation of attaching/detaching the male connector 7, as illustrated in FIGS. 1 and 7. The materials of the head portion 9 and the body portion 10 are not limited to those described above as long as the Young's modulus of the body portion 10 is larger than that of the head portion 9.

In addition, according to the present embodiment, the valve 3 includes the internal flow path 19 that passes through at least the body portion 10 and that allows the flow path 8 in the male connector 7 to communicate with the liquid flow path 6 in the open state, whereby the neutral structure can be more easily achieved.

According to the present embodiment, the internal flow path 19 is defined only by the inner surface of the valve 3, whereby the neutral structure can be more easily achieved. In addition, it is possible to suppress liquid retention in the medical connector 1.

According to the present embodiment, the internal flow path 19 has the open/close end 19a that passes through the head 9 portion and opens as the valve 3 moves down, whereby the neutral structure can be more easily achieved.

According to the present embodiment, the open/close end 19a is formed as the slit 14, whereby the neutral structure can be more easily achieved.

According to the present embodiment, the internal flow path 19 has the side end 19b that is open at the side face of the body portion 10, whereby the neutral structure can be more easily achieved.

According to the present embodiment, the liquid flow path 6 has the side opening 6a open at a side face defining the accommodation chamber 13 that accommodates the body portion 10 in a vertically movable manner, and the side opening 6a faces the side end 19b of the internal flow path 19 at least in the open state, whereby the neutral structure can be more easily achieved.

According to the present embodiment, the body portion 10 has the shoulder part 16 extending laterally from the bottom end of the head portion 9, whereby the neutral structure can be easily achieved with a simple structure.

According to the present embodiment, the body portion 10 has the upward protrusion 15 to which the bottom end of the head portion 9 is fitted, whereby the neutral structure can be easily achieved with a simple structure.

According to the present embodiment, the medical connector 1 includes the elastic member 4 that generates a biasing force, whereby the neutral structure can be easily achieved with a simple structure.

Figure 8:
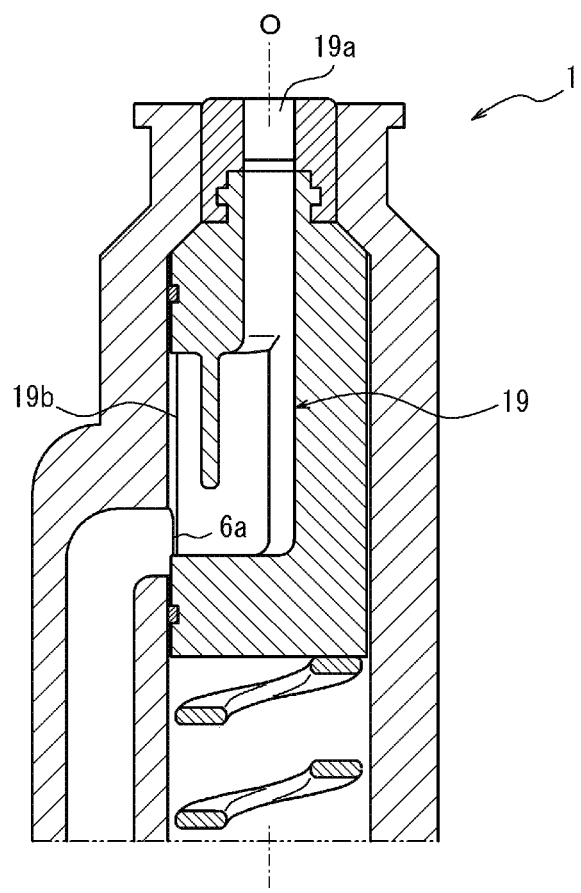
FIG. 8 is a cross-sectional view illustrating a medical connector as a second embodiment.
Figure 9:
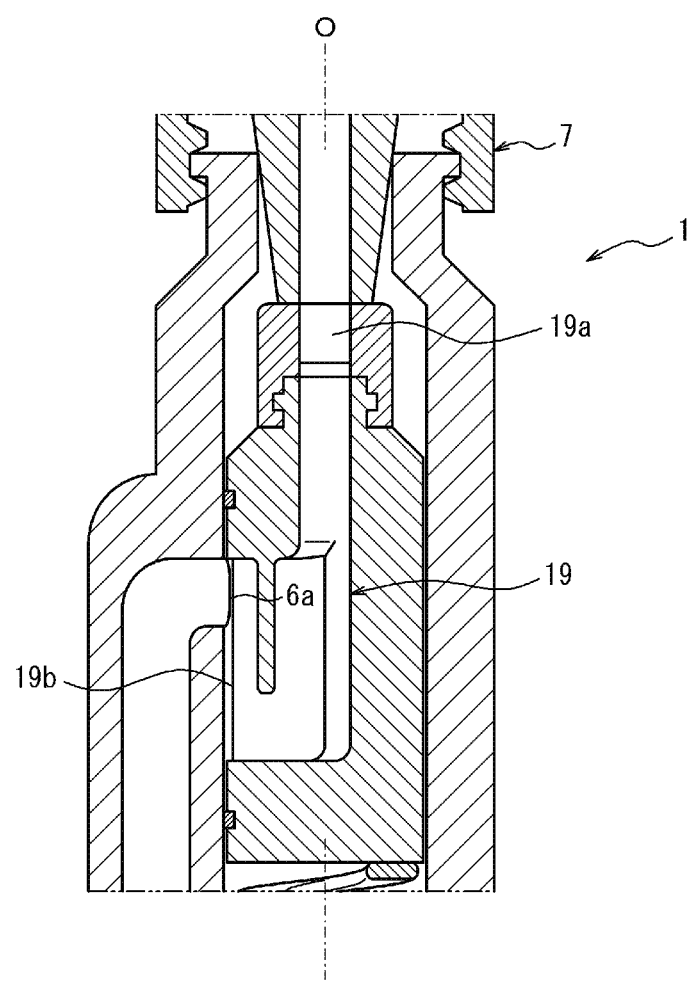
FIG. 9 is a cross-sectional view illustrating a state when a male connector is attached to the medical connector illustrated in FIG. 8.

Next, a medical connector 1 as a second embodiment will be described by way of example with reference to FIGS. 8 and 9. The medical connector 1 as the present embodiment illustrated in FIGS. 8 and 9 is different in configuration from the first embodiment only in that the upper portion of the side end 19b communicates with the open/close end 19a only through the lower portion of the side end 19b not facing the side opening 6a in the open state (see FIG. 9). The second embodiment can provide an effect of suppressing retention of liquid in the internal flow path 19 in addition to the effect obtained in the first embodiment.

Figure 10:
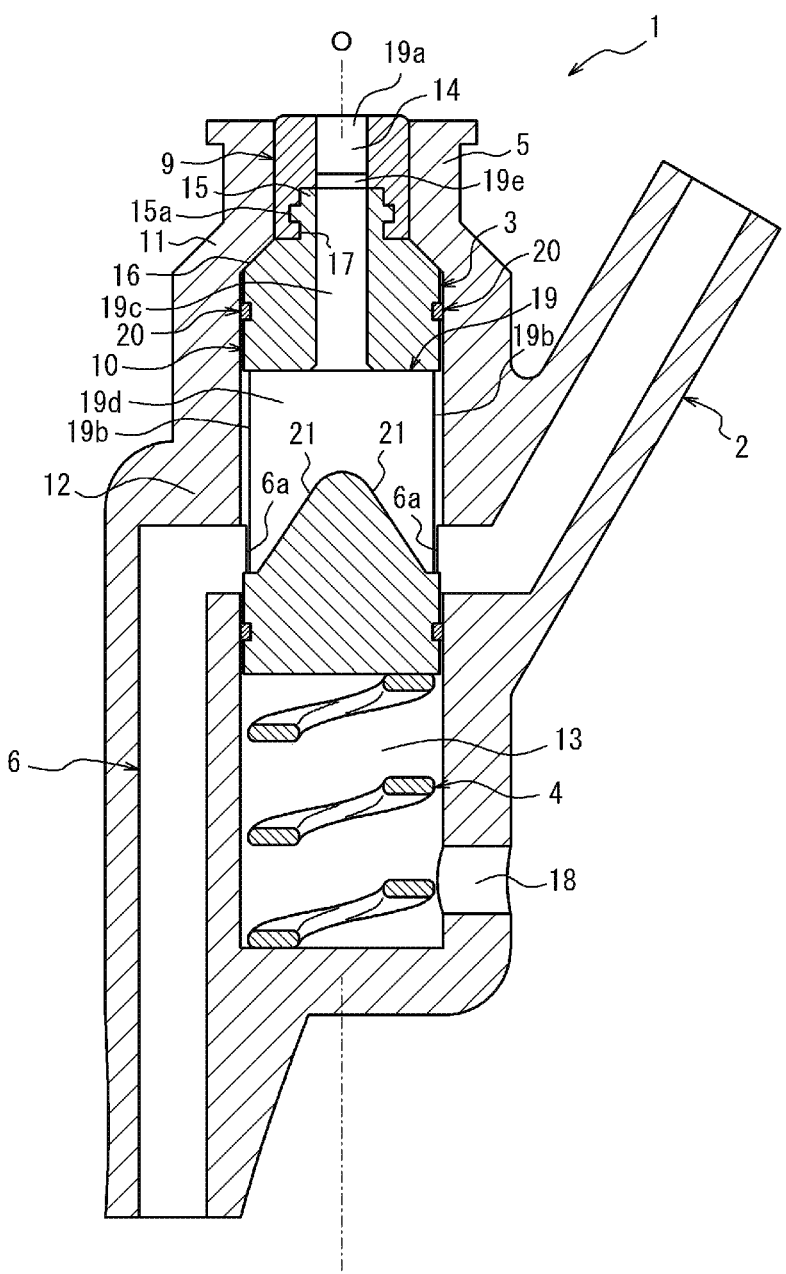
FIG. 10 is a cross-sectional view illustrating a medical connector as a third embodiment.
Figure 11:
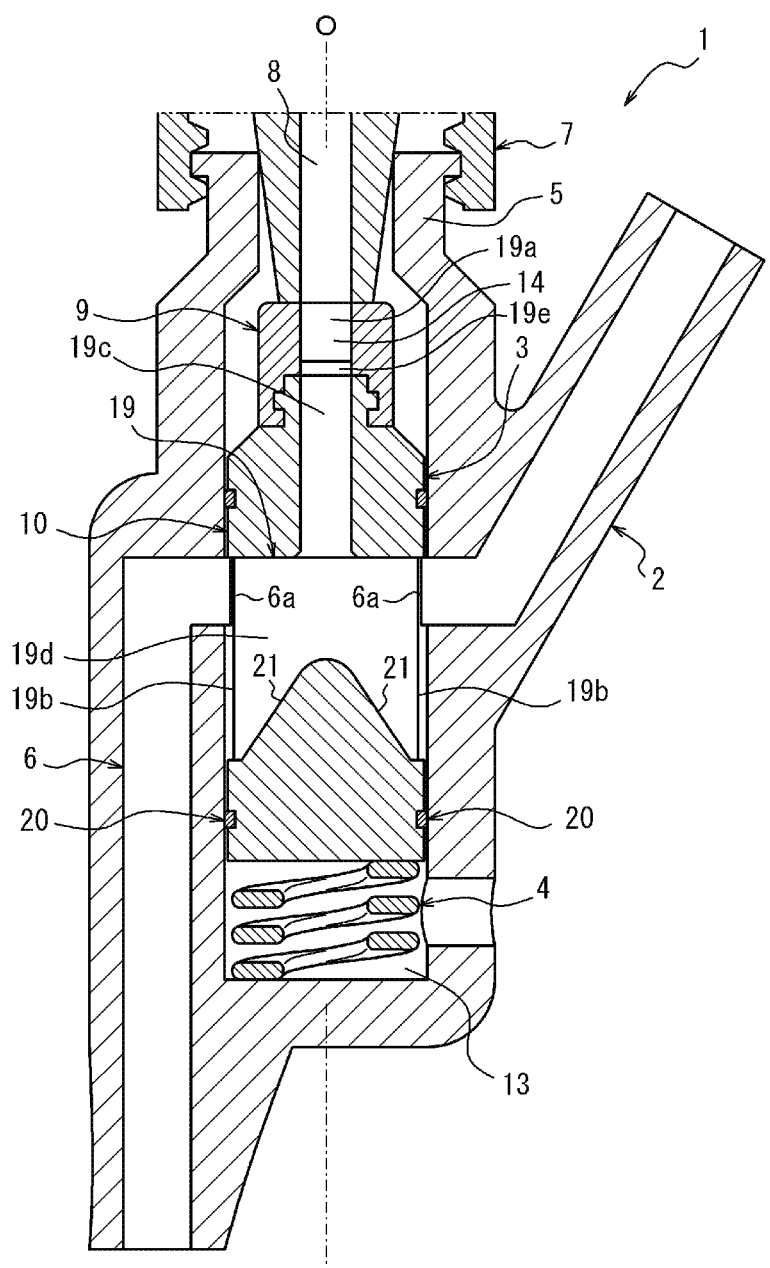
FIG. 11 is a cross-sectional view illustrating a state when a male connector is attached to the medical connector illustrated in FIG. 10.

Next, a medical connector 1 as a third embodiment will be described by way of example with reference to FIGS. 10 and 11. The medical connector 1 as the present embodiment illustrated in FIGS. 10 and 11 is different in configuration from the first embodiment in that the internal flow path 19 includes two side ends 19b open at the side face of the body portion 10, and the liquid flow path 6 includes two side openings 6a open at the side face defining the accommodation chamber 13. The other configurations are similar to those of the first embodiment.

One of the side ends 19b faces one of the side openings 6a in both the closed and the open state. The other side end 19b faces the other side opening 6a in both the closed state and the open state. The two side ends 19b are provided to be oriented in opposite directions.

The liquid flow path 6 has one flow path extending from the one of the side openings 6a and the other flow path extending from the other side opening 6a. The liquid flow path 6 is provided in the housing main body 12 of the housing 2.

The internal flow path 19 includes a longitudinal flow path 19c extending downward from the open/close end 19a and a lateral flow path 19d extending to both sides from the bottom end of the longitudinal flow path 19c. The lower surface of the lateral flow path 19d has a protruding shape formed by two inclined surfaces 21 inclined upward from the two side ends 19b toward the inside of the valve 3.

The body portion 10 has two seal members 20 surrounding the two side ends 19b. One of the seal members 20 surrounds the one of the side ends 19b, and the other seal member 20 surrounds the other side end 19b.

The third embodiment provides the following effects in addition to the effects obtained in the first embodiment.

According to the third embodiment, the internal flow path 19 includes the two side ends 19b, the liquid flow path 6 includes the two side openings 6a, one of the side ends 19b faces one of the side openings 6a in both the closed state and the open state, and the other side end 19b faces the other side opening 6a in both the closed state and the open state, and thus, the medical connector 1 can be used as a connector for mixed injection.

According to the third embodiment, the medical connector 1 in which the two side ends 19b are provided to be oriented in opposite directions can be achieved as a T-shaped connector or a Y-shaped connector.

According to the third embodiment, the internal flow path 19 includes the longitudinal flow path 19c extending downward from the open/close end 19a and the lateral flow path 19d extending to both sides from the bottom end of the longitudinal flow path 19c, and the lower surface of the lateral flow path 19d has a protruding shape formed by the two inclined surfaces 21 inclined upward from the two side ends 19b toward the inside of the valve 3, whereby the retention of the liquid in the internal flow path 19 can be prevented.

The above-described embodiments are merely an example of the present disclosure, and various modifications as described below, for example, are possible.

Various modifications are possible as long as the medical connector 1 includes: the housing 2 that is provided with the male connector attachment/detachment part 5 and forms the liquid flow path 6; and the valve 3 that is vertically movable with respect to the housing 2, between a closed position for closing the male connector attachment/detachment part 5 and an open position that allows the flow path 8 in the male connector 7 to communicate with the liquid flow path 6 by the valve 3 being pressed down from the closed position by the male connector 7 against a biasing force, wherein the valve 3 includes the head portion 9 that closes the male connector attachment/detachment part 5 when the valve 3 is in a closed state in which the valve 3 is at the closed position, and the body portion 10 that is connected to the bottom end of the head portion 9 and receives the biasing force, and the Young's modulus of the body portion 10 is larger than that of the head portion 9.

However, it is preferable that the valve 3 includes the internal flow path 19 that passes through at least the body portion 10 and allows the flow path 8 in the male connector 7 to communicate with the liquid flow path 6 in the open state in which the valve 3 is at the open position.

In addition, it is preferable that the internal flow path 19 is defined only by the inner surface of the valve 3.

It is preferable that the internal flow path 19 has the open/close end 19a that passes through the head portion 9 and opens as the valve 3 moves down.

It is preferable that the open/close end 19a is formed as the slit 14.

It is preferable that the internal flow path 19 has the side end 19b that is open at the side face of the body portion 10.

It is preferable that the liquid flow path 6 has the side opening 6a open at the side face defining the accommodation chamber 13 that accommodates the body 10 portion in a vertically movable manner, and the side opening 6a faces the side end 19b of the internal flow path 19 at least in the open state.

It is preferable that the upper portion of the side end 19b communicates with the open/close end 19a only through the lower portion of the side end 19b not facing the side opening 6a in the open state.

The internal flow path 19 includes two side ends 19b that are open at the side face of the body portion 10, the liquid flow path 6 includes two side openings 6a that are open at the side face defining the accommodation chamber 13 that accommodates the body 10 in a vertically movable manner, one of the two side ends 19b faces one of the two side openings 6a in both the closed state and the open state, and the other side end 19b faces the other side opening 6a in both the closed state and the open state.

The two side ends 19b are preferably provided to be oriented in opposite directions.

It is preferable that the internal flow path 19 includes the longitudinal flow path 19c extending downward from the open/close end 19a and the lateral flow path 19d extending to both sides from the bottom end of the longitudinal flow path 19c, and the lower surface of the lateral flow path 19d has a protruding shape formed by the two inclined surfaces 21 inclined upward from the two side ends 19b toward the inside of the valve 3.

The body 10 preferably has a shoulder part 16 extending laterally from the bottom end of the head portion 9.

The body 10 preferably has the upward protrusion 15 to which the bottom end of the head portion 9 is fitted.

The medical connector 1 preferably includes the elastic member 4 that generates a biasing force.

What is claimed is:

1. A medical connector comprising:
a housing comprising a male connector attachment/detachment part, the housing defining a liquid flow path; and
a valve that is vertically movable with respect to the housing between a closed position for closing the male connector attachment/detachment part, and an open position in which a flow path in a male connector communicates with the liquid flow path, by the valve being pressed down from the closed position by the male connector against a biasing force;
wherein:
the valve comprises a head portion that closes the male connector attachment/detachment part when the valve is at the closed position, and a body portion that is connected to a bottom end of the head portion and receives the biasing force, wherein the valve defines an internal flow path that passes through at least the body portion and allows the flow path in the male connector to communicate with the liquid flow path when the valve is at the open position, and the internal flow path has a side end that is open at a side face of the body portion; and
a Young's modulus of the body portion is larger than a Young's modulus of the head portion.

2. The medical connector according to claim 1, wherein:
the internal flow path is defined only by an inner surface of the valve.

3. The medical connector according to claim 1, wherein:
the internal flow path has an open/close end that passes through the head portion and opens as the valve moves down.

4. The medical connector according to claim 3, wherein:
the open/close end is formed as a slit.

5. The medical connector according to claim 1, wherein:
the housing defines an accommodation chamber that accommodates the body portion in a vertically movable manner;
the liquid flow path has a side opening that is open at a side face defining the accommodation chamber; and
the side opening faces the side end of the internal flow path at least when the valve is at the open position.

6. The medical connector according to claim 5, wherein:
an upper portion of the side end communicates with the open/close end only through a lower portion of the side end that does not face the side opening when the valve is at the open position.

7. The medical connector according to claim 1, wherein:
the body portion comprises a shoulder part extending laterally from the bottom end of the head portion.

8. The medical connector according to claim 1, wherein:
the body portion comprises an upward protrusion to which the bottom end of the head portion is fitted.

9. The medical connector according to claim 1, further comprising:
an elastic member that generates the biasing force.

10. A method of using a medical connector, the method comprising:
providing the medical connector, which comprises:
a housing comprising a male connector attachment/detachment part, the housing defining a liquid flow path, and
a valve comprising a head portion, and a body portion that is connected to a bottom end of the head portion, wherein the valve defines an internal flow path that passes through at least the body portion, and the internal flow path has a side end that is open at a side face of the body portion, and
a biasing member configured to provide a biasing force to the body portion of the valve so as to bias the valve to a closed position in which the male connector attachment/detachment part is closed by the head portion, wherein:
a Young's modulus of the body portion is larger than a Young's modulus of the head portion; and
attaching a male connector to the male connector attachment/detachment part such that the male connector presses the valve down from the closed position to an open position in which a flow path in the male connector communicates with the liquid flow path via the internal flow path.

11. A medical connector comprising:
a housing comprising a male connector attachment/detachment part, the housing defining a liquid flow path; and
a valve that is vertically movable with respect to the housing between a closed position for closing the male connector attachment/detachment part, and an open position in which a flow path in a male connector communicates with the liquid flow path, by the valve being pressed down from the closed position by the male connector against a biasing force;

wherein:

the valve comprises a head portion that closes the male connector attachment/detachment part when the valve is at the closed position, and a body portion that is connected to a bottom end of the head portion and receives the biasing force, wherein the valve defines an internal flow path that passes through at least the body portion and allows the flow path in the male connector to communicate with the liquid flow path when the valve is at the open position, and the internal flow path includes first and second side ends that are open at a side face of the body portion;

a Young's modulus of the body portion is larger than a Young's modulus of the head portion;

the housing defines an accommodation chamber that accommodates the body portion in a vertically movable manner;

the liquid flow path includes first and second side openings that are open at a side face defining the accommodation chamber;

the first side end faces the first side opening when the valve is at the closed position and when the valve is at the open position; and the second side end faces the second side opening when the valve is at the closed position and when the valve is at the open position.

12. The medical connector according to claim 11, wherein:

the internal flow path is defined only by an inner surface of the valve.

13. The medical connector according to claim 11, wherein:

the internal flow path has an open/close end that passes through the head portion and opens as the valve moves down.

14. The medical connector according to claim 13, wherein:

the open/close end is formed as a slit.

15. The medical connector according to claim 11, wherein:

the first and second ends are oriented in opposite directions.

16. The medical connector according to claim 15, wherein:

the internal flow path comprises a longitudinal flow path extending downward from the open/close end and a lateral flow path extending to the first and second side ends from a bottom end of the longitudinal flow path; and a lower surface defining the lateral flow path has a protruding shape formed by two inclined surfaces inclined upward and inward from the first and second side ends.

17. The medical connector according to claim 11, wherein:

the body portion comprises a shoulder part extending laterally from the bottom end of the head portion.

18. The medical connector according to claim 11, wherein:

the body portion comprises an upward protrusion to which the bottom end of the head portion is fitted.

19. The medical connector according to claim 11, further comprising:

an elastic member that generates the biasing force.

* * * * *